May 7, 1974 A. MEILLAND Plant Pat. 3,543
ROSE PLANT
Filed March 15, 1973
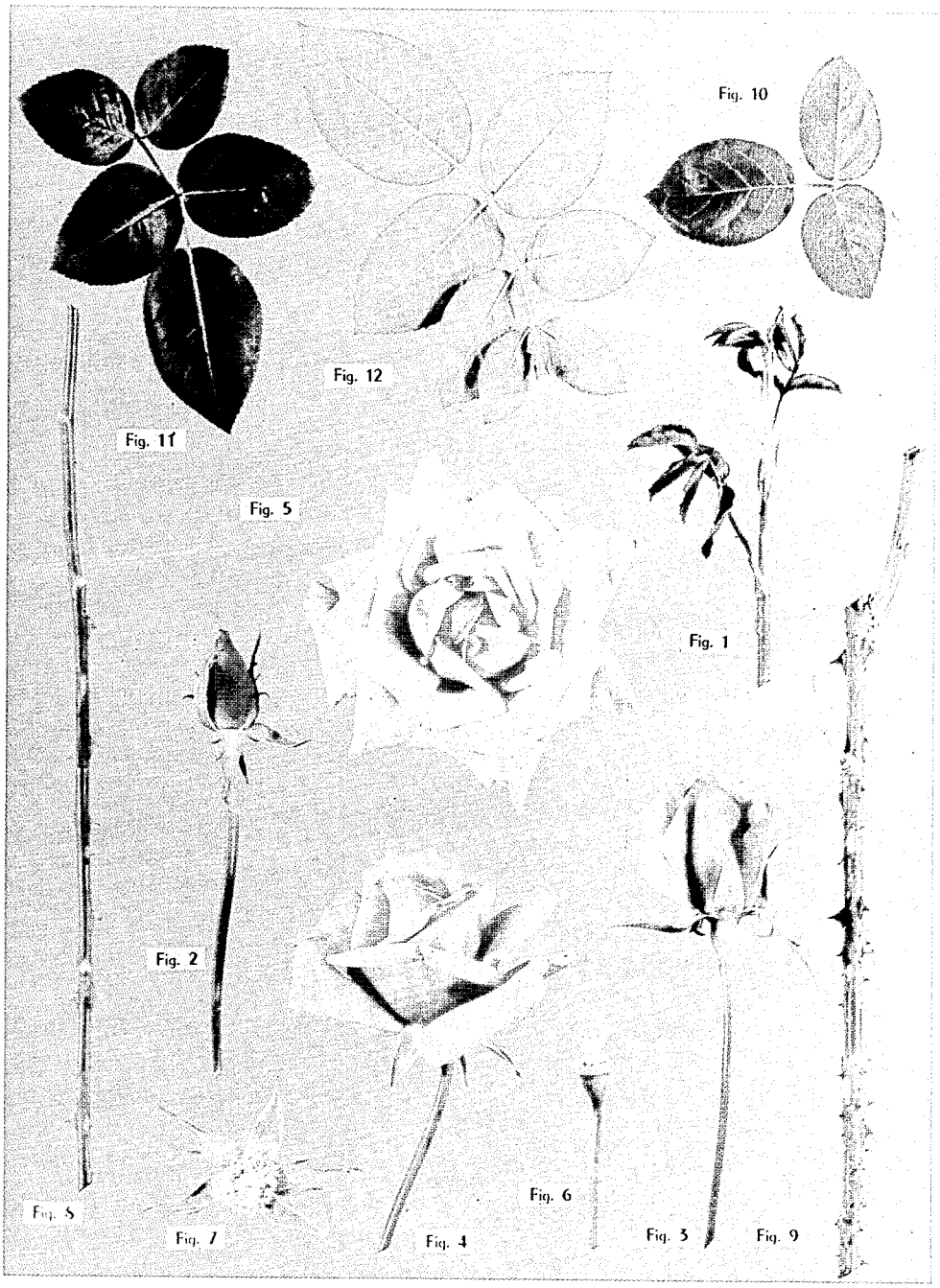

United States Patent Office

Plant Pat. 3,543
Patented May 7, 1974

3,543

ROSE PLANT

Alain Meilland, Cap d'Antibes, France, assignor to The Conard-Pyle Company, West Grove, Pa.

Filed Mar. 15, 1973, Ser. No. 341,463
Claims priority, application Morocco, Mar. 22, 1972, 16,035
Int. Cl. A01h 5/00
U.S. Cl. Plt.—18 1 Claim

ABSTRACT OF THE DISCLOSURE

A rose plant of the hybrid tea class, whose vegetative type corresponds to that of the variety Meichim 0257 F., more generally known in the trade as the rose Carina (U.S. Plant Pat. No. 2,378), but of a more even pink and less crimson color, with a pink color on the reverse side of the petals.

SUMMARY OF THE INVENTION

The present invention is a variety of rose plant, of the hybrid tea class, whose vegetative type corresponds to that of the variety Meichim 0257 F., more generally known in the trade under the name Carina (U.S. Plant Pat. No. 2,378), but whose flowers, although being of the same form, are of a more even pink, less crimson, which, with the pink coloring of the reverse side of the petals, shows a less pronounced contrast than the one existing in the aforesaid variety.

Considering the interest which, in the horticultural industry, would not fail to arise by the disclosure of the different technical effect offered by the new variety as compared with the original variety, it was advisable to multiply this new variety on a large scale in order to check its behavior from the physical as well as from the biological point of view.

The results were conclusive and emphasized the importance of the disclosure of such a variety with a view to its industrial exploitation by the professional nurserymen as well as by the producers of cut flowers.

The characteristics and properties of this new variety, obtained as indicated above, are thoroughly transmissible by agamic means—also called asexual means, i.e. by any method of vegetative propagation, and in particular by grafting an "eye," which will be called in the trade by the name "Kamchim eye" and which will be found on industrial plants as well as on the cut stems delivered subsequently in the trade.

BRIEF DESCRIPTION OF THE DRAWINGS

The accompanying drawings show typical specimens of the vegetative growth and flower of my new variety in different stages of development and as depicted in color as nearly true as it is reasonably possible to make the same in a color illustration of this character, and wherein:

FIG. 1 is a specimen of a young shoot;

FIG. 2 is a specimen of a bud when the sepals first open;

FIG. 3 is a specimen of a bud when the petals first open;

FIG. 4 is a specimen of a flower in the course of opening;

FIG. 5 is a specimen of a fully open flower, flat view;

FIG. 6 is a specimen of a receptacle showing the arrangement of the pistils atfer the stamens have been taken out;

FIG. 7 is a specimen of the disk of a receptacle showing the detail of the sepals and the arrangement of the stamens and of the pistils;

FIG. 8 is a portion of a flowering stem;

FIG. 9 is a portion of a main branch;

FIG. 10 is a specimen of a leaf with three leaflets, upper surface;

FIG. 11 is a specimen of a leaf with five leaflets, upper surface; and

FIG. 12 is a specimen of a leaf with seven leaflets, under surface.

DETAILED DESCRIPTION OF DISCLOSURE

The following is a detailed description of my new variety in which the terminology of the colors corresponds to that of the Horticultural Colour Chart of the Royal Horticultural Society:

Class: Hybrid tea.

Plant:

*Height.*—75 to 85 cms. in the open air; 1.20 m. to 1.40 m. under glass.

*Habit.*—straight, well branched.

Branches:

*Color.*—Young stems: Spinach Green (p. 187–0960/2) with a light Lettuce Green (p. 176–861/1) reflection close to the stipules. Mature wood: Spinach Green (p. 187–0960/1).

*Prickles.*—Shape: straight. Size: medium. Quantity: fairly numerous and intermixed with acicules. Color: on young stems: slightly reddish, then greenish; on mature wood: light havana color (common terms).

Leaves:

*Stipules.*—Adnate—generally narrow—with folded edges, more or less pectinate; the auricles are short and diverging.

*Petiole.*—Obverse: the inside and the edges of the rib are more or less reddish brown in the young foliage, and normal green in the adult foliage. Reverse: light green—generally with one or several small curved prickles.

*Leaflets.*—Number: 3–5 and 7. Shape: elliptical—acuminate. Teeth: single. Texture: leathery. General effect: fairly wide foliage, of average density, and dull appearance. Color—young foliage—upper surface: Spinach Green p. 187—a little darker than 0960; under surface: Lavender Green p. 196—a little "rawer" green than 000761/1; adult foliage—upper surface: Spinach Green, p. 187–0960; under surface: Lavender Green, p. 196–000761/1

(It is to be noted that when growth starts, as also during the course of vegetation, the foliage of the young shoots is light green and reddish brown on the upper surface; reddish brown on the under surface. The outer skin of the tigelias is Lettuce Green (p. 176–861/1.))

Inflorescence:

*Number of flowers.*—Generally one flower per stem.

*Peduncle.*—Very firm—light Green—with a few tiny prickles, without consistence. Length: 12 to 14 cms. (under glass).

*Sepals.*—Normal—the inside is hairy, greenish white; the outside is light green.

*Bracts.*—Sometimes, the base of the peduncle has bracts, especially in the exceptional case when the stems bear 2 or 3 flowers.

*Bud.*—Shape: pointed—fairly elongated. Length: 3 cms. ½ out of the calyx—open sepals. Size: medium. Color—inside: Carmine rose, p. 75, intermediate between 621/1 and 621, with Tone 621 in the veins. Outside: Rose Madder, p. 23, tone 23/1 more or less mottled with 23.

*Flower.*—Form: full and high-centered, then somewhat globular; finally overlapping when open, with center more or less covered up: double. Diameter: 12 cms. on an average. Color: when opening—inside: Carmine rose, p. 75 621/1 on the edges—621 in depth; Outside: Rose Madder, p. 23 23/1 more or less mottled with 23. During the course of opening: Inside: Neyron Rose, p. 76 623/1 on the surface, 623 in the veins; Outside: Rose Madder, p. 23 23/2, more or less spotted with 23/1. When fully open: Inside: Neyron Rose, p. 76 623/2 on the rim, 623/1 in depth; outside: Rose Madder, p. 23 23/3 more or less spotted with 23/2.

*Fragrance.*—light.

*Duration.*—Very long lasting, either on the plant, or when cut.

*Corolla.*—Petals—texture: very firm. Shape: well rounded, then progressively with edges folded in a point, especially on the exterior periphery. The center ones are not always entire; they are often fairly strongly blistered and cover up more or less the stamens. The unguis is yellowish white. Number: 45 on an average, 4 or 5 of which, in the center, are not entire. The petals drop off cleanly. Stamens—number: average 160; anthers: normal pale yellow; filaments: uneven in height; the longest ones are yellowish, the shortest ones light fuchsine. Pistils—number: 130 on an average; stigmas: normal—yellowish; styles: emerging more or less freely from a thick collar of silky hairs. They are greenish yellow at the base; light fuchsine near the stigmas.

*Receptacle.*—As a tube more or less pyriform or funnel-shaped. It is light green.

Development:

*Vegetation.*—Vigorous.

*Blooming.*—Continuous.

*Aptitude for setting fruit.*—Rather weak.

*Resistance to frosts.*—Spring—normal. Winter—strong resistance.

*Resistance to diseases.*—Blackspot: very good. Mildew: very good. Powdery mildew: very good. Rust: very good.

I claim:

1. A new and distinct variety of rose plant of the hybrid tea class, characterized by the novelty of the plant, from the physical point of view, in that the plant, with Spinach Green mature wood, is of straight habit, the flower is double, Rose Neyron colored, its petals are very firm and folded up in a point when fully open, and from the biological point of view, the plant grows vigorously, blooms continuously, has a very good resistance to fungus diseases, its flowers are very long lasting, either on the plant or when cut, and their petals drop off cleanly.

No references cited.

ROBERT E. BAGWILL, Primary Examiner